US008721996B2

(12) United States Patent
Hechler et al.

(10) Patent No.: US 8,721,996 B2
(45) Date of Patent: May 13, 2014

(54) REACTOR FOR CONTINUOUS HETEROGENEOUSLY CATALYZED PARTIAL DEHYDROGENATION OF AT LEAST ONE HYDROCARBON TO BE DEHYDROGENATED

(75) Inventors: Claus Hechler, Ludwigshafen (DE); Wilhelm Ruppel, Mannheim (DE); Goetz-Peter Schindler, Ludwigshafen (DE); Catharina Klanner, Mannheim (DE); Hans-Juergen Bassler, Neustadt (DE); Martin Dieterle, Mannheim (DE); Karl-Heinrich Klappert, Birkenheide (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 934 days.

(21) Appl. No.: 12/841,211

(22) Filed: Jul. 22, 2010

(65) Prior Publication Data

US 2010/0286461 A1 Nov. 11, 2010

Related U.S. Application Data

(62) Division of application No. 11/614,425, filed on Dec. 21, 2006, now Pat. No. 7,790,942.

(60) Provisional application No. 60/751,973, filed on Dec. 21, 2005.

(30) Foreign Application Priority Data

Dec. 21, 2005 (DE) .......................... 10 2005 061 626

(51) Int. Cl.
*B01J 8/00* (2006.01)

(52) U.S. Cl.
USPC ........... 422/641; 422/632; 422/634; 422/651; 422/652; 422/240; 422/241

(58) Field of Classification Search
USPC ......... 422/641, 632, 634, 651, 652, 655, 240, 422/241; 148/325, 327, 335; 420/43, 94, 420/100
See application file for complete search history.

(56) References Cited

U.S. PATENT DOCUMENTS

| 3,784,373 | A | | 1/1974 | Ornitz et al. | |
| 4,224,062 | A | * | 9/1980 | Darnfors | 420/40 |
| 4,444,731 | A | * | 4/1984 | Konoki et al. | 422/310 |
| 5,693,155 | A | | 12/1997 | Mousseaux et al. | |
| 5,705,684 | A | | 1/1998 | Hefner et al. | |
| 5,997,826 | A | * | 12/1999 | Lodeng et al. | 422/634 |
| 6,419,986 | B1 | | 7/2002 | Holtermann et al. | |
| 6,426,433 | B1 | | 7/2002 | Machhammer et al. | |
| 6,676,906 | B1 | * | 1/2004 | Heisel | 422/601 |
| 6,781,017 | B2 | | 8/2004 | Machhammer et al. | |
| 6,890,393 | B2 | * | 5/2005 | Buck | 148/325 |
| 7,238,827 | B2 | | 7/2007 | Hechler et al. | |
| 2003/0040570 | A1 | | 2/2003 | Nestler et al. | |
| 2003/0044334 | A1 | | 3/2003 | Kadowaki et al. | |
| 2003/0187299 | A1 | | 10/2003 | Machhammer et al. | |
| 2004/0176657 | A1 | | 9/2004 | Abdulwahed et al. | |
| 2004/0181083 | A1 | | 9/2004 | Proll et al. | |
| 2004/0199001 | A1 | | 10/2004 | Schindler et al. | |
| 2005/0118088 | A1 | * | 6/2005 | Olbert et al. | 423/416 |
| 2005/0119515 | A1 | | 6/2005 | Machhammer et al. | |
| 2006/0004226 | A1 | | 1/2006 | Machhammer et al. | |
| 2007/0088092 | A1 | | 4/2007 | Klanner et al. | |

FOREIGN PATENT DOCUMENTS

| DE | 102 45 585 A1 | 4/2004 |
| DE | 103 16 039 A1 | 10/2004 |
| DE | 10 2004 032 129 A1 | 3/2005 |
| DE | 10 2005 051 401 A1 | 4/2007 |
| EP | 0 718 415 A1 | 6/1996 |
| EP | 0 731 077 A2 | 9/1996 |
| EP | 0 799 169 | 10/1997 |
| FR | 2 175 755 | 10/1973 |
| JP | 8-218152 | 8/1996 |
| JP | 8-245494 | 9/1996 |
| JP | 2002-523390 | 7/2002 |
| WO | 96/19424 | 6/1996 |
| WO | 00/10961 | 3/2000 |
| WO | 01/96270 A2 | 12/2001 |
| WO | 01/96271 A2 | 12/2001 |
| WO | 03/011804 A2 | 2/2003 |
| WO | 03/076370 A1 | 9/2003 |

* cited by examiner

*Primary Examiner* — Nina Bhat
(74) *Attorney, Agent, or Firm* — Oblon, Spivak, McClelland, Maier & Neustadt, L.L.P.

(57) ABSTRACT

A shell which encloses an interior and has at least one first orifice for feeding at least one gas stream into the interior and at least one second orifice for withdrawing a gas stream fed to the interior beforehand via the at least one first orifice from the interior, the surface of the shell, on its side in contact with the interior, being manufactured at least partly, in a layer thickness of at least 1 mm, from a steel which has a specific elemental composition, and in the interior, a process for continuous heterogeneously catalyzed partial dehydrogenation of at least one hydrocarbon to be dehydrogenated is carried out in a reactor which is manufactured from the steel on its side in contact with the reaction gas.

16 Claims, No Drawings

REACTOR FOR CONTINUOUS HETEROGENEOUSLY CATALYZED PARTIAL DEHYDROGENATION OF AT LEAST ONE HYDROCARBON TO BE DEHYDROGENATED

This is a divisional application of U.S. application Ser. No. 11/614,425, filed Dec. 21, 2006, which claims benefit of 601751,973 filed on Dec. 21, 2005, now U.S. Pat. No. 7,790,942.

The present invention relates to a process for continuous heterogeneously catalyzed partial dehydrogenation of at least one hydrocarbon to be dehydrogenated in the gas phase, comprising a procedure in which a reaction chamber which is enclosed by a (material) shell which is in contact with the reaction chamber and has at least one first orifice for feeding at least one starting gas stream into the reaction chamber and at least one second orifice for withdrawing at least one product gas stream from the reaction chamber, at least one starting gas stream comprising at least one hydrocarbon to be dehydrogenated is fed continuously, in the reaction chamber, the at least one hydrocarbon to be dehydrogenated is passed through at least one catalyst bed disposed in the reaction chamber and, with generation of a product gas comprising the at least one dehydrogenated hydrocarbon, unconverted hydrocarbon to be dehydrogenated and molecular hydrogen and/or steam, is dehydrogenated partially in an oxidative or nonoxidative manner to at least one dehydrogenated hydrocarbon, and at least one product gas stream is withdrawn continuously from the reaction chamber.

The present invention also relates to an apparatus for carrying out the process according to the invention, and to processes for partial oxidation of the at least one dehydrogenated hydrocarbon.

The term "dehydrogenated hydrocarbon" used in this application is intended to comprise hydrocarbons whose molecules comprise at least two ("two" are preferred from an application point of view) hydrogen atoms fewer than the molecules of a hydrocarbon to be dehydrogenated Otherwise, the term hydrocarbon is intended to comprise substances whose molecules are formed only from the elements carbon and hydrogen.

Hence dehydrogenated hydrocarbons comprise especially acyclic and cyclic aliphatic hydrocarbons having one or more C, C double bonds in the molecule.

Examples of such aliphatic dehydrogenated hydrocarbons are propene, isobutene, ethylene, 1-butene, 2-butene and butadiene. In other words, the dehydrogenated hydrocarbons include in particular the monounsaturated linear hydrocarbons (n-alkenes) or branched aliphatic hydrocarbons (e.g. isoalkenes), and also the cycloalkenes. Moreover, the dehydrogenated hydrocarbons are also intended to comprise the alkapolyenes (e.g. dienes and trienes) which comprise more than one carbon-carbon double bond in the molecule. However, dehydrogenated hydrocarbons are also intended to comprise hydrocarbon compounds which are obtainable starting from alkylaromatics such as ethylbenzene or isopropylbenzene by dehydrogenation of the alkyl substituents. These are, for example, compounds such as styrene or α-methylstyrene.

Dehydrogenated hydrocarbons are quite generally valuable starting compounds for the synthesis of, for example, functionalized, free-radically polymerizable compounds (e.g. acrylic acid from propene or methacrylic acid from isobutene and polymerization products thereof). For example, such functionalized compounds can be obtained by partial oxidation of dehydrogenated hydrocarbons. However, dehydrogenated hydrocarbons are also suitable for preparing compounds such as methyl tert-butyl ether (subsequent product of isobutene, which is suitable, for example, as a fuel additive for increasing the octane number). Dehydrogenated hydrocarbons may also be used as such for polymerization themselves.

Useful hydrocarbons to be dehydrogenated in this document are especially the acyclic and cyclic alkanes, but also olefins (whose C, C double bond number is to be increased) (as an example, mention should be made of the heterogeneously catalyzed partial dehydrogenation of n-butenes to butadiene).

In other words, the term "hydrocarbons to be dehydrogenated" in this patent application comprises, for example, hydrocarbons of the stoichiometry $C_n H_{2n+2}$ where n>1 to n≤20, and of the stoichiometry $C_n H_{2n}$ where n>1 to n≤20, and of the stoichiometry $C_n H_{2n-2}$ where n>2 to n≤20, and n=an integer, especially $C_2$- to $C_{16}$-alkanes, for example ethane, propane (to propylene), n-butane, isobutane (to isobutene), n-pentane, isopentane, n-hexane, n-heptane, n-octane, n-nonane, n-decane, n-undecane, n-dodecane, n-tridecane, n-tetradecane, n-pentadecane and n-hexadecane.

In particular, however, all statements made in this document apply to $C_2$- to $C_8$-alkanes as hydrocarbons to be dehydrogenated and very particularly to $C_2$ to $C_4$ hydrocarbons (in particular alkanes). In other words, hydrocarbons to be dehydrogenated in this document are in particular ethane, propane, n-butane and isobutane, but also 1-butene and 2-butene.

The process described at the outset for preparing dehydrogenated hydrocarbons is common knowledge (cf., for example, WO 03/076370, DE-A 10 2004 032 129, EP-A 731 077, WO 01/96271, WO 01/96270, DE-A 103 16 039, WO 03/011804, WO 00/10961, EP-A 799 169 and DE-A 102 45 585).

In principle, the processes for preparing dehydrogenated hydrocarbons by heterogeneously catalyzed partial dehydrogenation of at least one hydrocarbon to be dehydrogenated are divided into two groups: oxidative and nonoxidative heterogeneously catalyzed partial dehydrogenations. In contrast to the oxidative heterogeneously catalyzed partial dehydrogenation, the nonoxidative heterogeneously catalyzed partial dehydrogenation is effected without the action of molecular oxygen. In other words, the molecular hydrogen to be pulled from the hydrocarbon to be dehydrogenated is pulled out immediately as molecular hydrogen and is also not oxidized at least partly oxidatively to water with molecular oxygen in a subsequent step. The thermal character of a nonoxidative dehydrogenation is thus endothermic in every case. In the oxidative heterogeneously catalyzed partial dehydrogenation, in contrast, the molecular hydrogen to be pulled from the hydrocarbon to be dehydrogenated is pulled out under the action of molecular oxygen. It can be pulled out immediately as water ($H_2O$) (this case is also referred to for short as a heterogeneously catalyzed oxydehydrogenation; its thermal character is exothermic in every case). However, it can also be done initially as molecular hydrogen (i.e. nonoxidatively or conventionally) which can then be oxidized partly or fully with molecular oxygen to water ($H_2O$) in a subsequent step (depending on the extent of subsequent hydrogen combustion, the overall thermal character may be endothermic, exothermic or neutral).

It is common to all aforementioned heterogeneously catalyzed partial dehydrogenations of hydrocarbons to be dehydrogenated that they proceed at comparatively high reaction temperatures. Typical reaction temperatures may be ≥250° C., frequently ≥300° C., often ≥350° C., or ≥400° C., or ≥450° C., or ≥500° C.

In the course of long-term operation of a continuous heterogeneously catalyzed partial dehydrogenation, moreover, even higher reaction temperatures are normally required increasingly with the operating time, in order to maintain the dehydrogenation conversion in single pass through the reaction chamber. This is typically because the catalysts used become irreversibly deactivated to an increasing extent with increasing operating time. In other words, even when the continuous operation is interrupted temporarily time and again (such an operating mode is intended to be comprised by the term "continuously" in this document), in order to reactivate (to regenerate) the catalysts used by means of suitable measures, the original activity of the catalysts with the overall operating time is increasingly long attained with increasing overall operating time of the process. Corresponding increase in the reaction temperature can counteract this fact.

A disadvantage of such high reaction temperatures is that, relative to the desired target reaction (hydrocarbon to be dehydrogenated→dehydrogenated hydrocarbon), undesired side reactions gain increasing weight to an extent generally increasing with the reaction temperature. One of these undesired side reactions is, for example, the thermal decomposition of the hydrocarbon to be dehydrogenated and/or of the dehydrogenated hydrocarbon, typically to hydrocarbons having a smaller number of carbon atoms.

The material recommended for the shell in processes described at the outset in the prior art are various steels. WO 03/076370 recommends, for example, as a material for the shell in its working examples, steel which has been alonized, alitized and/or aluminized (i.e. coated with aluminum, or with aluminum oxide, or with aluminum and aluminum oxide) on the side of the shell in contact with the reaction chamber. No further statements regarding the composition of the steel are made by WO 03/076370. The same recommendation is made by WO 03/011804. As a possible alternative, it additionally recommends the use of sulfides in the starting gas stream for the purpose of passivating the side of the shell in contact with the reaction chamber.

However, a disadvantage of an alonization or alitization and/or alumination is that it can be carried out on the industrial scale only at exceptional cost. A disadvantage of use of sulfides in the starting gas stream is firstly the demand therefor and secondly that such a use generally has an adverse effect on the lifetime of the catalysts used for the heterogeneously catalyzed partial dehydrogenation and/or an adverse effect on the lifetime of the catalysts used for a heterogeneously catalyzed partial oxidation of the dehydrogenated hydrocarbon which follows if appropriate.

The aforementioned disadvantages are not possessed by the teaching of DE-A 10 2004 032 129 which recommends, as the material for the shell in its comparative example, uncoated stainless steel of DIN materials number 1.4841. In a similar manner, DE-A 10 2005 051 401 and DE-A 102005052917 recommend Si-containing stainless steel or steel in a quite general sense, for example that of DIN type 1.4841, as a material for the shell.

However, in-house investigations have found that, surprisingly, steel, as a material for the side of the shell in contact with the reaction chamber, is capable of catalyzing the thermal decomposition of hydrocarbons to be dehydrogenated and/or of dehydrogenated hydrocarbons, as a result of which they become noticeable in an undesired manner even at comparatively low reaction temperatures. This applies not least to the stainless steel of DIN materials number 1.4841 which may have the following elemental composition:

from 24 to 26% by weight of Cr,
from 19 to 22% by weight of Ni,
from 1.5 to 2.5% by weight of Si,
from ≥0 to ≤0.11% by weight of N,
from ≥0 to ≤0.2% by weight of C,
from ≥0 to 2% by weight of Mn,
from ≥0 to 0.045% by weight of P,
from ≥0 to 0.015% by weight of S, and
apart from these Fe and impurities resulting from the production, the percentages each being based on the total weight.

Normally, the nitrogen content of this steel type is significantly less than 0.11% by weight and is generally not specified for this reason on the part of the steel producers.

In the course of in-house investigations, it has also been found that the catalytic action of a steel on the thermal decomposition of hydrocarbons to be dehydrogenated and/or dehydrogenated hydrocarbons is dependent upon the elemental composition of the steel used.

A disadvantage of a thermal decomposition of hydrocarbon to be dehydrogenated and/or dehydrogenated hydrocarbon is not just that such a thermal decomposition lowers the target product selectivity but also that the resulting decomposition products, at elevated temperature, are all potential formers of elemental carbon (coke) which is capable of being deposited on the surface of the catalysts used for the heterogeneously catalyzed partial dehydrogenation, in order thus to deactive them at an accelerated rate and at least partly even irreversibly. In addition, a thermal decomposition of hydrocarbons fundamentally proceeds endothermically and withdraws heat from the actual target reaction.

It was therefore an object of the present invention to provide a process as described at the outset using a steel suitable for the surface of the shell on its side in contact with the reaction chamber, which, even in nonalonized form and also in the absence of sulfides in the starting gas stream, catalyzes the thermal decomposition of hydrocarbon to be dehydrogenated and/or dehydrogenated hydrocarbon in a less marked manner than stainless steel of DIN materials number 1.4841.

Accordingly, a process has been found for continuous heterogeneously catalyzed partial dehydrogenation of at least one hydrocarbon to be dehydrogenated in the gas phase, comprising a procedure in which a reaction chamber which is enclosed by a (material) shell which in contact with the reaction chamber (i.e. in contact with the reaction gas, i.e. the hydrocarbon to be dehydrogenated and the dehydrogenated hydrocarbon) and has at least one first orifice for feeding at least one starting gas stream into the reaction chamber and at least one second orifice for withdrawing at least one product gas stream from the reaction chamber, at least one starting gas stream comprising at least one hydrocarbon to be dehydrogenated is fed continuously, in the reaction chamber, the at least one hydrocarbon to be dehydrogenated is passed through at least one catalyst bed disposed in the reaction chamber and, with generation of a product gas comprising the at least one dehydrogenated hydrocarbon, unconverted hydrocarbon to be dehydrogenated and molecular hydrogen and/or steam, is dehydrogenated partially in an oxidative or nonoxidative manner to at least one dehydrogenated hydrocarbon, and at least one product gas stream is withdrawn continuously from the reaction chamber, wherein the surface of the shell, on its side in contact with the reaction chamber, is manufactured at least partly, in a layer thickness d of at least 1 mm (in each case pointing away from the reaction chamber at right angles to the tangent applied to the particular point of contact on the side in contact with the reaction chamber), from a steel S which has the following elemental composition:

from 18 to 30% by weight of Cr,
from 9 to 36% by weight of Ni,
from 1 to 3% by weight of Si,
from 0.1 to 0.3% by weight of N,
from ≥0, preferably from 0.03 to 0.15% by weight of C,
from ≥0 to 4% by weight of Mn,
from ≥0 to 4% by weight of Al,
from ≥0 to 0.05% by weight of P,
from ≥0 to 0.05% by weight of S, and
from ≥0 to 0.1, preferably from >0 to 0.1 and more preferably from 0.03 to 0.08% by weight of one or more rare earth metals, and, apart from these, Fe and impurities resulting from production, the percentages each being based on the total weight (of the steel).

In the context of the aforementioned contents, it is preferred quite generally when the content of N is ≥0.11, better ≥0.12, preferably ≥0.13, more preferably ≥0.14 and even better ≥0.15% by weight. More preferably, the N content is from 0.15 to 0.18% by weight. More preferably, the ranges specified as preferred above are employed in combination.

Advantageously in accordance with the invention, the total amount of the impurities resulting from the production are, quite generally and on the same basis, ≤1% by weight, preferably ≤0.75% by weight, more preferably ≤0.5% by weight and most preferably ≤0.25% by weight. However, the total amount of impurities resulting from the production of the steel will generally be ≥0.1% by weight. In contrast to the impurities resulting from the production, the other constituents of the steel are certain alloy constituents which determine its properties. This applies especially to the elements Cr, Ni, Si, N and C.

The rare earth metals comprise the elements cerium (Ce), praseodymium (Pr), neodymium, (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu). The rare earth metal preferred in accordance with the invention is Ce. Preferably in accordance with the invention, the relevant steel S therefore has from ≥0 to 0.1% by weight of Ce or Ce and one or more rare earth metals other than Ce (especially La, Nd and/or Pr).

Advantageously in accordance with the invention, the surface of the shell (the wall surrounding the reaction chamber), on its side in contact with the reaction chamber, is manufactured to an extent of at least 10%, preferably to an extent of at least 20%, or to an extent of at least 30%, even more preferably to an extent of at least 40%, or to an extent of at least 50%, even more advantageously to an extent of at least 60% or to an extent of at least 70%, better to an extent of at least 80% or to an extent of at least 90% and at best to an extent of at least 95% or to an extent of at least 100% of its total surface area, in a layer thickness d of at least 1 mm, from the relevant steel. Advantageously in accordance with the invention, the aforementioned d is at least 2 mm, or at least 3 mm, or at least 4 mm, or at least 5 mm. It will be appreciated that d may also be from ≥5 mm to 30 mm, or up to 25 mm, or up to 20 mm, or up to 15 mm, or up to 10 mm. Most preferably, the shell enclosing the reaction chamber in the process according to the invention is manufactured in its entirety or to an extent of at least 80% of its weight, better to an extent of at least 90% or to an extent of at least 95% of its weight, from the inventive steel. Preferably in accordance with the invention, the (pipe)lines conducting the at least one starting gas stream to the reaction chamber and the at least one product gas stream away from the reaction chamber are manufactured from the inventive steel S, or coated with such a steel at least on their side in contact with gas. Of course, these (pipe)lines (especially those leading away) may also be manufactured from other steels, for example of DIN materials numbers 1.4910, or 1.4941, or 1.4541 or 1.4841. The use of the inventive steels S is of increased relevance especially when reaction gas comes into contact with material which has a temperature of ≥450° C.

For proper and safe operation, the aforementioned (pipe) lines are preferably equipped with devices for compensating longitudinal expansion effects, as can occur, for example, owing to temperature changes, and it is advantageous to use compensators which feature a lateral mode of action.

These compensators which generally have a multilayer design may be manufactured from the same material as the pipeline itself. However, particularly advantageous embodiments are those with (generally: gas-permeable rigid inner tube and gas-impermeable elastic outer sleeve (gas-impermeable elastic outer tube)) an inner tube part, preferably manufactured from an inventive steel S, which is in contact with the gas to be conducted and appropriately has a gas-permeable expansion joint and an external, gas-impermeable, elastic, corrugated part which is manufactured at least partly from an especially mechanically and thermally stressable material, for example material 1.4876 (designation according to VdTÜV-Wb 434) or 1.4958/1.4959 (designation according to DIN 17459) or INCOLOY® 800 H or 800 HT, or nickel-base material 2.4816 (alternative designation Alloy 600) or 2.4851 (alternative designation Alloy 601).

Preferably in accordance with the invention, the steel S relevant in accordance with the invention has the following elemental composition:

from 18 to 26% by weight of Cr,
from 9 to 36% by weight of Ni,
from 1 to 2.5% by weight of Si,
from 0.1 to 0.3% by weight of N,
from ≥0, preferably (irrespective of the other contents) from 0.03 to 0.15% by weight of C,
from ≥0 to 3% by weight of Mn,
from ≥0 to 4% by weight of Al,
from ≥0 to 0.05% by weight of P,
from ≥0 to 0.05% by weight of S, and
from ≥0 to 0.1, preferably from >0 to 0.1 and more preferably from 0.03 to 0.08% (in each case irrespective of all other contents) by weight of one or more rare earth metals (preferably Ce or Ce and one or more other rare earth metals), and, apart from these, Fe and impurities resulting from production, the percentages each being based on the total weight (of the steel).

More advantageously, the steel S relevant in accordance with the invention has the following elemental composition:

from 20 to 25% by weight of Cr,
from 9 to 20 or (irrespective of the other contents) preferably to 15% by weight of Ni,
from 1.4 to 2.5% by weight of Si,
from 0.1 to 0.3% by weight of N,
from ≥0, preferably (irrespective of the other contents) from 0.03 to 0.15% by weight of C,
from ≥0 to 3% by weight of Mn,
from ≥0 to 4% by weight of Al,
from ≥0 to 0.05% by weight of P,
from ≥0 to 0.05% by weight of S, and
from ≥0 to 0.1, preferably from >0 to 0.1 and more preferably from 0.03 to 0.08% (in each case irrespective of all other contents) by weight of one or more rare earth metals (preferably Ce or Ce and one or more other rare earth metals), and, apart from these, Fe and impurities resulting from production, the percentages each being based on the total weight (of the steel).

More preferably, the steel S relevant in accordance with the invention has the following elemental composition:
from 20 to 22% by weight of Cr,
from 10 to 12% by weight of Ni,
from 1.4 to 2.5% by weight of Si,
from 0.12 to 0.2% by weight of N,
from ≥0, preferably (irrespective of all other contents) from 0.05 to 0.12% by weight of C,
from ≥0 to 1% by weight of Mn,
from ≥0 to 2, preferably (irrespective of all contents) 0% by weight of Al,
from ≥0 to 0.045% by weight of P,
from ≥0 to 0.015% by weight of S, and
from ≥0 to 0.1, preferably from >0 to 0.1 and more preferably from 0.03 to 0.08% (in each case irrespective of all other contents) by weight of one or more rare earth metals (preferably Ce or Ce and one or more other rare earth metals), and, apart from these, Fe and impurities resulting from production, the percentages each being based on the total weight (of the steel).

Quite generally, it is favorable in the context of all compositions mentioned above as advantageous or preferred when the content of N is ≥0.11, better ≥0.12, preferably ≥0.13, more preferably ≥0.14 and even better ≥0.15% by weight. Particular preference is given in all cases to an N content of from 0.15 to 0.18% by weight. Advantageously, all ranges mentioned as preferred in each case are employed in combination.

It is essential to the invention that, in particular, the preferred steel compositions S are already selected such that they are found to be advantageous not just in relation to the undesired catalytic action of the relevant steel.

Instead, in particular, the selection of the preferred ranges made additionally takes into account that the steel selected as the material additionally has to be found to be highly advantageous also with regard to its mechanical stressability and with regard to its corrosion stress and other wear stress. This fact is of significance especially when the shell is manufactured substantially fully from the selected steel S.

For example, the steel S used should also have a low embrittlement tendency under the process conditions to be employed for the heterogeneously catalyzed partial dehydrogenation. This is especially true at the elevated reaction temperatures to be employed normally in the process according to the invention. This is true in particular when the reaction temperatures and/or catalyst regeneration temperatures are from ≥400° C. to ≤900° C., or from ≥500° C. to ≤800° C., or from ≥550° C. to ≤750° C., or from ≥600° C. to ≤700° C. The aforementioned requirement also already takes into account that the process according to the invention for heterogeneously catalyzed partial dehydrogenation is preferably carried out at working pressures above 1 atm. in other words, the steel S to be used in accordance with the invention should also be suitable as a pressure vessel material. Moreover, the creep strength and thermal stability characteristics of the steel selected in accordance with the invention should be satisfactory under the conditions of the process according to the invention. The same applies to its scaling resistance and to its coking tendency. The advantageous selection made also takes into account that the steel selected has to be processible in an advantageous manner. This means in particular that it has to be processible with welding technology, which is not possible in the case of steels alonized prior to the processing without impairment of the alonization. However, alonization after processing can be performed on the industrial scale only with a very high level of cost and inconvenience, if at all. The requirement for corrosion resistance is of significance especially from the aspect that the dehydrogenated hydrocarbon formed in the process according to the invention can be partially oxidized under heterogeneous catalysis in a process which follows the process according to the invention (particularly advantageously accompanied by the undehydrogenated hydrocarbon). When the desired partial oxidation product is removed subsequently from the product gas mixture of the partial oxidation, a residual gas comprising hydrocarbon yet to be dehydrogenated and oxygenates normally remains and is advantageously recycled at least partly into the process according to the invention for the purpose of further conversion of the hydrocarbon yet to be dehydrogenated. However, corrosive action is attributable to the overwhelming majority of all oxygenates (for example acrolein, acrylic acid, methacrolein, methacrylic acid, $H_2O$, $O_2$, $CO_2$ etc.).

The steels S suitable in accordance with the invention are producible in a manner known per se. See, for example, the remarks in Enzyklopädie Naturwissenschaft und Technik [Encyclopedia of Natural Science and Technology], Verlag moderne Industrie, 1976, under the headings "Stahlbegleiter", "Eisen" and "Eisen und Stahl" ["Steel constituents", "Iron" and "Iron and Steel"], or Ullmanns Encyclopädie der technischen Chemie [Ullmann's Encyclopedia of Industrial Chemistry], Verlag Chemie, 4th edition, volume 3, Verfahrenstechnik II und Reaktionsapparate [Process Technology II and Reaction Apparatus], chapter "Werkstoffe in der chemischen Industrie" ["Materials in the Chemical Industry"].

Steels suitable in accordance with the invention are, for example, the steels of EN materials numbers 1.4818, 1.4835 and 1.4854, among which very particular preference is given to those of materials number 1.4835. Also suitable for the process according to the invention are the steels of DIN materials numbers 1.4891 and 1.4893, of which preference is given to those having the materials number 1.4893. Also suitable for the process according to the invention are steels of ASTM/UNS materials numbers S 30415, S 30815 and S 35315, among which preference is given in accordance with the invention to those with the materials number S 30815. Also suitable for the process according to the invention are steels with the SS materials numbers 2372, 2361 and 2368, among which preference is given in accordance with the invention to the latter.

Aforementioned and other steels suitable in accordance with the invention are also commercially available. For example, Outokumpu Stainless AB, in SE-774 22 Avesta, Sweden sells the aforementioned steels under its own designations 153 MA™, 253 MA® and 353 MA®, among which 253 MA® is particularly advantageous in accordance with the invention. ThyssenKrupp Nirosta GmbH, in D-47794 Krefeld, Germany likewise sells a steel particularly favorable in accordance with the invention with the alloyed stainless steel THERMAX® 4835.

The steels S suitable in accordance with the invention thus include in particular steels of the compositions:
I. 18.5% by weight of Cr,
9.5% by weight of Ni,
1.3% by weight of Si,
0.15% by weight of N,
from ≥0 to ≤0.05% by weight of C,
from ≥0 to ≤1% by weight of Mn,
from ≥0 to ≤0.045% by weight of P,
from ≥0 to ≤0.015% by weight of S, and
from ≥0 to 0,1, preferably from >0 to 0.1 and more preferably from 0.03 to 0.08% by weight of one or more rare earth metals (preferably Ce or Ce and one or more other rare earth metals), and, apart from these, Fe and impurities resulting from production, the percentages each being based on the total weight.

II. 21% by weight of Cr,
11% by weight of Ni,
from 1.4 to 2.5% by weight of Si,
0.17% by weight of N,
0.09% by weight of C,
from $\geq 0$ to $\leq 1$% by weight of Mn,
from $\geq 0$ to $\leq 0.045$% by weight of P,
from $\geq 0$ to $\leq 0.015$% by weight of S, and
from $\geq 0$ to 0.1, preferably from $>0$ to 0.1 and
more preferably from 0.03 to 0.08% by weight of one or more rare earth metals (preferably Ce oder Ce and one or more other rare earth metals), and, apart from these, Fe and impurities resulting from production, the percentages each being based on the total weight.

III. from 24 to 26% by weight of Cr,
from 34 to 36% by weight of Ni,
from 1.2 to 2.0% by weight of Si,
from 0.12 to 0.2% by weight of N,
from 0.04 to 0.08% by weight of C,
from $\geq 0$ to $\leq 2.0$% by weight of Mn,
from $\geq 0$ to $\leq 0.045$% by weight of P,
from $\geq 0$ to $\leq 0.015$% by weight of S, and
from $\geq 0$ to 0.1, preferably from $>0$ to 0.1 and
more preferably from 0.03 to 0.08% by weight one or more rare earth metals (preferably Ce oder Ce and one or more other rare earth metals), and, apart from these, Fe and impurities resulting from the production, the percentages each being based on the total weight.

Of course, the steels S suitable in accordance with the invention can also be used for the process according to the invention in alonized, alitized and/or aluminized form (especially on their side in contact with the reaction chamber). In this form too, they are found to be particularly advantageous in that, where the alonization is damaged, for example as a result of the manufacture, or becomes damaged, only a slight catalytic action on the thermal decomposition comes into effect.

When the shell in the process according to the invention is not to be manufactured fully from steel suitable in accordance with the invention, but rather, the surface of the shell is to be manufactured only partly or fully from such steel on its side in contact with the reaction chamber in the inventive minimum layer thickness (for example, it may be appropriate for reasons of economic viability to manufacture the surface of the shell, on its side in contact with the reaction chamber, in accordance with the invention, only where particularly high temperatures occur in the reaction chamber, or indeed to manufacture only the surface from inventive steel in the inventive minimum layer thickness), this is possible in a simple manner, for example, by plating (for example roller plating, or explosive plating, or compression weld plating), i.e. by applying the inventive steel as a cover material to the surface of another base material (for example another steel) at the desired points or over the entire surface, and bonding it firmly to the base material, for example, by pressing, or rolling, or adhesive bonding or welding.

The process according to the invention is advantageous especially when the at least one starting stream comprises steam (for example $\geq 1$% by volume) as an inert diluent gas and/or molecular oxygen (for example $\geq 0.1$ or $\geq 0.5$% by volume) as a reactant. However, it is also advantageous when the at least one starting stream comprises steam and/or molecular oxygen as impurities. It is also advantageous when, in the course of the inventive heterogeneously catalyzed partial dehydrogenation, steam is formed as a reaction product. This is especially true when the cycle gas or loop method recommended in WO 03/076370 is employed for the process according to the invention. However, the process according to the invention is particularly advantageous not least when the at least one starting gas stream comprises residual gas which stems from a partial oxidation of dehydrogenated hydrocarbon formed in the process according to the invention connected downstream of the process according to the invention, accompanied by hydrocarbon yet to be dehydrogenated, remains after target product removal from the product gas mixture of the partial oxidation and comprises oxygenate.

Quite generally, the at least one catalyst bed disposed in the reaction chamber may be either a fluidized bed or a moving bed or a fixed bed. Of course, fluidized bed and, for example, fixed bed, or moving bed and fixed bed, may also be present in combination in the reaction chamber. Preferably in accordance with the invention, the at least one catalyst bed of the process according to the invention comprises exclusively fixed catalyst beds.

In this document, the loading of a catalyst bed catalyzing a reaction step with reaction gas should be understood quite generally to mean the amount of reaction gas in standard liters (=l (STP); the volume in liters that the corresponding amount of reaction gas would take up under standard conditions (0° C., 1 atm)) which is conducted through one liter of catalyst bed (for example fixed catalyst bed) per hour. However, the loading may also be based only on one constituent of the reaction gas. In that case, it is the amount of this constituent in l (STP)/l·h which is conducted through one liter of the catalyst bed per hour (pure inert material beds are not counted in a fixed catalyst bed). The loading may also be based only on the amount of catalyst present in one catalyst bed which comprises the actual catalyst diluted with inert material (this is then stated explicitly).

In this document, a full oxidation (combustion) of a dehydrogenated hydrocarbon and/or hydrocarbon to be dehydrogenated is understood to mean that the total amount of carbon present in the hydrocarbon is converted to oxides of carbon ($CO$, $CO_2$). All different conversions of a dehydrogenated hydrocarbon and/or hydrocarbon to be dehydrogenated with the reactive action of molecular oxygen are encompassed in this document with the term partial oxidation. The additional reactive action of ammonia is a feature of ammoxidation, which is likewise encompassed under the term partial oxodation.

In this document, an inert gas should be understood generally to mean a reaction gas constituent which behaves substantially chemically inertly under the conditions of the appropriate reaction and, each inert reaction gas constituent taken alone, remains chemically unchanged to an extent of more than 95 mol %, preferably to an extent of more than 97 mol % or to an extent of more than 99 mol %. Examples of typically inert diluent gases are, for example, $N_2$, $H_2O$, $CO_2$, nobel gases such as Ne and Ar, and mixtures of these gases, etc.

When the process according to the invention is a heterogeneously catalyzed oxydehydrogenation (for example that of propane to propylene), the source used for the molecular oxygen required therefor may be air, pure molecular oxygen or air enriched in molecular oxygen.

The need to perform the process according to the invention over selective dehydrogenation catalysts in the solid state is caused by the dehydrogenation (splitting of C—H) being kinetically disfavored compared to thermal cleavage or cracking (splitting of C—C). Owing to the selective catalysts and with use of an inventive reaction chamber, by-products such as methane, ethylene and ethane are formed only in minor amounts in the case of an inventive heterogeneously catalyzed dehydrogenation of propane.

In this document, a dehydrogenation catalyst should therefore be understood to mean in particular a shaped body whose longest dimension L (longest direct line connecting two points present on the surface of the shaped body) is from 0.1 or 1 to 30 mm, preferably from 1 to 20 mm and more preferably from 1 to 10 mm or from 1 to 5 mm, and which, in the experiment described below, based on single pass of the reaction mixture through the reaction tube, dehydrogenates at least 5 mol % of the propane present in the reaction gas to propylene:

A reaction tube made of steel to be used in accordance with the invention of EN materials number 1.4835 with a wall thickness of 2 mm and an internal diameter of 35 mm and a length of 80 cm is charged as follows. 50 ml of a bed of the appropriate dehydrogenation catalyst are placed centrally in the reaction tube. Above and below the bed of shaped catalyst bodies, the reaction tube is filled up in each case with a bed of steatite spheres (inert spheres) having a sphere diameter of from 1.5 mm to 2.5 mm. A grid bears the entire bed. From the outside, the reaction tube is kept at a temperature of 550° C. over its entire length. The reaction tube is charged with a mixture of propane and steam in a volume ratio of 2 (propane) to 1 (steam) with a propane loading of the catalyst bed of 1000 l (STP)/l·h. The starting gas stream has been preheated to a temperature of 550° C. Particular preference is given to dehydrogenation catalysts in which the cumulative selectivity of the formation of the ethane, ethylene and methane by-products under the aforementioned boundary conditions is ≤5 mol %, based on converted propane.

An inventive heterogeneously catalyzed oxydehydrogenation can in principle be carried out in such a way as described, for example, in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086, 032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B. V., p. 305-313, 3$^{rd}$ World Congress on Oxidation Catalysis, R. K. Grasselli, S. T. Oyama, A. M. Gaffney and J. E. Lyons (Ed.), 1997, Elsevier Science B. V., p. 375ff or in DE-A 198 37 520, DE-A 198 37 517, DE-A 198 37 519 and DE-A 198 37 518, using the example of the heterogeneously catalyzed partial oxydehydrogenation of propane. In this case, as already stated, the oxygen source used may, for example, be air. However, the oxygen source used, in addition to inert gas, here frequently has molecular oxygen to an extent of at least 90 mol %, and in many cases molecular oxygen to an extent of at least 95 mol %.

The catalysts suitable for the heterogeneously catalyzed oxydehydrogenation are subject to no particular restrictions. Suitable oxydehydrogenation catalysts are all of those which are known to those skilled in the art in this field and are capable, for example, of oxidizing propane to propylene. In particular, all oxydehydrogenation catalysts mentioned in the aforementioned documents may be used. Suitable catalysts are, for example, oxydehydrogenation catalysts which comprise MoVNb oxides or vanadyl pyrophosphate, if appropriate with promoter. One example of a favorable oxydehydrogenation catalyst is a catalyst which comprises a mixed metal oxide I with Mo, V, Te, O and X as essential constituents, where X is at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (on this subject, see also EP-A 938463 and EP-A 167109). Further particularly suitable oxydehydrogenation catalysts are the multimetal oxide compositions or catalysts A (referred to in this document as multimetal oxide compositions II) of DE-A-197 53 817 and the catalysts of DE-A 19838312, the multimetal oxide compositions or catalysts A mentioned as preferred in the former document being very particularly favorable. Thus, useful active compositions for an inventive heterogeneously catalyzed oxydehydrogenation include multimetal oxide compositions of the general formula III

$$M^1{}_a Mo_{1-b} M^2{}_b O_x \quad (III)$$

where
M$^1$=Co, Ni, Mg, Zn, Mn and/or Cu,
M$^2$=W, V, Te, Nb, P, Cr, Fe, Sb, Ce, Sn and/or La,
a=0.5-1.5,
b=0-0.5, and
x=a number which is determined by the valency and the frequency of the elements in (III) other than oxygen.

They can be prepared and shaped as described in DE-A 102 45 585.

For a heterogeneously catalyzed oxydehydrogenation of propane for example, the reaction temperature when fresh catalysts are used is preferably in the range from 200 to 600° C., in particular in the range from 250 to 500° C., more preferably in the range from 350 to 440° C. The working pressure is preferably in the range from 0.5 to 10 bar, in particular from 1 to 10 bar, more preferably from 1 to 5 bar. Working pressures above 1 bar, for example from 1.5 to 10 bar, have been found to be particularly advantageous. In general, the heterogeneously catalyzed oxydehydrogenation of propane is effected over a fixed catalyst bed. The latter is appropriately introduced (generally disposed on a gas-permeable grid) into the tubes (the tube wall together with the two tube orifices forms the shell in contact with the reaction chamber; the tube interior is the reaction chamber; the tube wall is preferably manufactured entirely from inventive steel) of a, for example, salt bath-cooled tube bundle reactor, as described, for example, in EP-A 700 893 and in EP-A 700 714 and in the literature cited in these documents. The starting gas stream is fed to the tube inlet. The mean residence time of the reaction gas in the catalyst bed is appropriately from 0.5 to 20 seconds. The ratio of propane to oxygen varies with the desired conversion and the selectivity of the catalyst. It is appropriately in the range from 0.5:1 to 40:1, in particular from 1:1 to 6:1, more preferably from 2:1 to 5:1. In general, the propylene selectivity decreases with increasing propane conversion. Preference is therefore given to carrying out the propane-to-propylene reaction in such a way that relatively low conversions with propane are achieved at high selectivities for propylene. More preferably, the conversion of propane is in the range from 5 to 40 mol %, frequently in the range from 10 to 30 mol %. In this context, the term "propane conversion" means the proportion of propane fed which is converted in single pass of the reaction gas through the tube. In general, the selectivity of propylene formation is from 50 to 98 mol %, more preferably from 80 to 98 mol %, the term "selectivity" meaning the moles of propylene which are obtained per mole of propane converted, expressed as the molar percentage. In the reaction tube, the reaction temperature generally passes through a maximum.

In general, the starting gas stream used in a heterogeneously catalyzed propane oxydehydrogenation comprises from 5 to 95 mol % of propane (based on 100 mol % of starting gas). In addition to propane and oxygen, the starting gas for the heterogeneously catalyzed oxydehydrogenation may also comprise further, especially inert, constituents such as carbon dioxide, carbon monoxide, nitrogen, noble gases, other hydrocarbons, present, for example, in crude propane (the propane source used for the process according to the invention is normally crude propane as recommended, for example, in DE-A 10245585 or DE-A 102005022798), and/or propylene. The heterogeneously catalyzed oxydehydrogenation may also be carried out in the presence of diluents, for example steam.

Any desired reactor sequence known to those skilled in the art may be used to carry out the heterogeneously catalyzed oxydehydrogenation of propane, for example. For example, the heterogeneously catalyzed oxydehydrogenation may be carried out in a single reactor or in a battery of two or more reactors, between which oxygen is fed if appropriate.

As possible constituents, the product gas of an inventive heterogeneously catalyzed propane dehydrogenation may comprise, for example, the following constituents: propylene (as the target product, i.e. as the dehydrogenated hydrocarbon), propane (as the unconverted hydrocarbon to be dehydrogenated), carbon dioxide, carbon monoxide, water, nitrogen, oxygen, ethane, ethene, methane, acrolein, acrylic acid, ethylene oxide, butane (e.g. n-butane or isobutane), acetic acid, formaldehyde, formic acid, propylene oxide and butenes (e.g. butene-1). Especially the ethane, ethene and methane are possible thermal decomposition products of propane. Typically, a product gas obtained in an inventive heterogeneously catalyzed propane oxydehydrogenation comprises: from 5 to 10 mol % of propylene, from 0.1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 2 mol % of acetic acid, from 0.01 to 0.05 mol % of formaldehyde, from 1 to 5 mol % of oxygen, from 0.1 to 10 mol % of further constituents mentioned above, and also substantially propane as the remainder, based in each case on 100% product gas.

Heterogeneously catalyzed oxydehydrogenations or hydrocarbons other than propane to be dehydrogenated may be carried out in accordance with the invention in a corresponding manner, as described above for the oxydehydrogenation of propane. Useful such hydrocarbons to be oxydehydrogenated are in particular butane (to butene (in particular isobutane to isobutene) and/or butadiene) and also butenes (to butadiene).

The regeneration of catalysts used for a partial heterogeneously catalyzed oxydehydrogenation of propane, for example, can be undertaken as described for partial oxidation catalysts in the documents DE-A 103 51 269, DE-A 103 50 812 and DE-A 103 50 822.

When the inventive heterogeneously catalyzed partial dehydrogenation is not an oxydehydrogenation, it always includes a conventional heterogeneously catalyzed dehydrogenation, i.e. molecular hydrogen is formed at least as an intermediate and, in the case of an oxidative (conventional) heterogeneously catalyzed partial dehydrogenation, is at least partly combusted in a subsequent step with molecular oxygen to give water.

Useful catalysts for a heterogeneously catalyzed conventional dehydrogenation of hydrocarbons to be dehydrogenated in the process according to the invention are in principle all dehydrogenation catalysts known in the prior art for conventional heterogeneously catalyzed dehydrogenations. They can be divided roughly into two groups, specifically into those which are of oxidic nature (for example chromium oxide and/or aluminum oxide) and into those which consist of at least one generally comparatively noble metal (for example platinum) deposited on a generally oxidic support. The dehydrogenation catalysts which may be used thus include all of those which are recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105, U.S. Pat. No. 3,670,044, U.S. Pat. No. 6,566,573, U.S. Pat. No. 4,788,371, WO 94/29021 and DE-A 199 37 107. In particular, the catalyst according to Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the periodic table of the elements, lanthanum and/or tin, with the proviso that the sum of the percentages adds up to 100% by weight.

Generally, the dehydrogenation catalysts may be catalyst extrudates (diameter typically from 0.1 or 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). For a heterogeneously catalyzed dehydrogenation in a fluidized bed (or moving bed), more finely divided catalyst will accordingly be used. Preference is given in accordance with the invention to the fixed catalyst bed.

In general, the dehydrogenation catalysts (especially those recommended in DE-A 199 37107 (especially the exemplary catalysts of this DE-A)) are such that they are capable of catalyzing both the dehydrogenation of the hydrocarbon to be dehydrogenated (e.g. propane) and the combustion of the hydrocarbon to be dehydrogenated (e.g. propane) and of molecular hydrogen. The hydrogen combustion proceeds very much more rapidly over the catalysts both in comparison to the dehydrogenation of the hydrocarbon to be dehydrogenated (e.g. propane) and in comparison to its combustion in the case of a competition situation.

Useful reactor types and process variants for an inventive conventional heterogeneously catalyzed partial dehydrogenation of a hydrocarbon to be dehydrogenated (e.g. propane) are in principle all of those known in the prior art, provided that the reaction chamber in the particular reactor fulfills the inventive profile of requirements. Descriptions of such process variants are present, for example, in all prior art documents cited with regard to the dehydrogenation catalysts and the prior art cited at the outset of this document.

A comparatively comprehensive description of processes also suitable for inventive reaction chambers for conventional heterogeneously catalyzed dehydrogenation (non-oxidative or oxidative) is present, for example, in Catalytica® Studies Division, Oxidative Dehydogenation and Alternative Dehydrogenation Processes, Study Number 4192 OD, 1993, 430 Ferguson Drive, Mountain View, Calif., 94043-5272 U.S.A.

It is characteristic of the conventional partial heterogeneously catalyzed dehydrogenation of hydrocarbons to be dehydrogenated (e.g. propane) that the dehydrogenation step proceeds endothermically. This means that the heat (energy) required for the attainment of the required reaction temperature has to be supplied to the reaction gas either beforehand and/or in the course of the heterogeneously catalyzed dehydrogenation.

In other words, based on single pass of the at least one starting stream through the at least one catalyst bed in the reaction chamber with the inventive properties, the reaction chamber can be configured isothermically (externally controlled temperature profile) by controlled heat exchange with, for example, fluid (i.e. liquid or gaseous) heat carriers conducted outside the reaction chamber enclosed by the inventive shell. Corresponding heat exchangers may also be accommodated in the reaction chamber itself.

However, with the same reference basis, it can also be designed adiabatically, i.e. substantially without such controlled heat exchange with (externally) conducted heat carriers (externally uncontrolled temperature profile). In the latter case, the gross thermal character based on single pass through the inventive reaction chamber, by an internally controlled (for example by hydrogen combustion in a subsequent step) temperature profile yet to be described below, may be configured either endothermically (negative) or autothermally (essentially zero) or exothermically (positive).

Typically, an inventive conventional heterogeneously catalyzed partial dehydrogenation of at least one hydrocarbon to be dehydrogenated (for example of propane) requires, as already mentioned, comparatively high reaction temperatures. The achievable conversion is normally restricted by the thermodynamic equilibrium. Typical reaction temperatures are from 300 to 800° C., or from 400 to 700° C. Per molecule of, for example, propane dehydrogenated to propylene, one molecule of hydrogen is obtained. High temperatures and removal of the $H_2$ reaction product shift the equilibrium position toward the target product, as does partial pressure reduction by inert dilution.

In addition, it is typical for conventional heterogeneously catalyzed partial dehydrogenations of at least one hydrocarbon to be dehydrogenated (for example of propane), owing to the high reaction temperatures required, that small amounts of high-boiling high molecular weight organic compounds, up to and including carbon, are formed and are deposited on the catalyst surface, thus deactivating it. In order to minimize this disadvantageous phenomenon, the starting gas which comprises the hydrocarbon to be dehydrogenated (for example the propane) and is to be passed at elevated temperature over the catalyst surface for the conventional heterogeneously catalyzed dehydrogenation can be diluted with steam. Carbon which is deposited is eliminated partly or fully and continuously under the resulting conditions by the principle of coal gasification.

Another means of eliminating deposited carbon compounds consists in flowing a gas comprising oxygen through the dehydrogenation catalyst at elevated temperature from time to time and thus to effectively burn off the deposited carbon. However, a certain suppression of the formation of carbon deposits is also possible by adding molecular hydrogen to the hydrocarbon to be dehydrogenated in a conventional manner under heterogeneous catalysis (for example propane) before it is conducted over the dehydrogenation catalyst at elevated temperature.

It will be appreciated that the possibility also exists of adding a mixture of steam and molecular hydrogen to the hydrocarbon to be dehydrogenated under heterogeneous catalysis (for example propane). Addition of molecular hydrogen to the heterogeneously catalyzed dehydrogenation of propane also reduces the undesired formation of allene (propadiene), propyne and acetylene as by-products.

It may therefore be appropriate in accordance with the invention (as already addressed) to carry out the conventional heterogeneously catalyzed hydrocarbon (e.g. propane) dehydrogenation (for example with comparatively low propane (or generally hydrocarbon) conversion) (quasi-)adiabatically. This means that the starting gas will generally first be heated to a temperature of from 400 or 500 to 700° C. (of from 550 to 650° C.) (for example by direct firing of the wall surrounding it). Normally, a single adiabatic pass through at least one catalyst bed disposed in the inventive reaction chamber will be sufficient to achieve the desired conversion, in the course of which the reaction gas will cool by from about 30° C. to 200° C. (depending on conversion and dilution). Presence of steam as a heat carrier is also noticeably advantageous from the point of view of an adiabatic method. The comparatively low reaction temperature enables longer lifetimes of the catalyst bed used.

In principle, an inventive conventional heterogeneously catalyzed hydrocarbon (e.g. propane) dehydrogenation (irrespective of whether conducted adiabatically or isothermally) can be carried out either in a fixed catalyst bed or in a moving bed or fluidized bed.

Suitable catalyst charges for a conventional heterogeneously catalyzed dehydrogenation of a hydrocarbon to be dehydrogenated (e.g. propane) with a comparatively low conversion as described in single pass through the inventive reaction chamber are especially the catalysts disclosed in DE-A 199 37 107, in particular disclosed by way of example, and their mixtures with geometric shaped bodies which are inert with respect to the conventional heterogeneously catalyzed dehydrogenation.

After prolonged operating time, the aforementioned catalysts can be regenerated in a simple manner, for example, by initially passing air (preferably) diluted with nitrogen and/or steam in first regeneration stages through the (fixed) catalyst bed at an inlet temperature of from 300 to 600° C. (in extreme cases, if appropriate, even to 750° C.), frequently from 400 to 550° C. The catalyst loading with regeneration gas may (based on the total amount of catalyst regenerated) be, for example, from 50 to 10,000 $h^{-1}$ and the oxygen content of the regeneration gas from 0.5 to 20% by volume.

In subsequent further regeneration stages, the regeneration gas used under otherwise identical regeneration conditions may be air. Appropriately from an application point of view, it is recommended to flush the catalyst with inert gas (i.e. $N_2$) before it is regenerated.

Subsequently, it is generally advisable to regenerate with pure molecular hydrogen or with molecular hydrogen diluted with inert gas (preferably steam and/or nitrogen) (the hydrogen content should be ≥1% by volume) under otherwise identical conditions.

A conventional heterogeneously catalyzed hydrocarbon (e.g. propane) dehydrogenation in the process according to the invention may be operated both at low ≤30 mol %) and at high (≥30 mol %) conversion of hydrocarbon to be dehydrogenated (e.g. propane) in the inventive reaction chamber at catalyst loadings (based on the total amount of catalyst used) both with starting gas and with hydrocarbon to be dehydrogenated present therein (e.g. propane) of from 100 to 10,000 $h^{-1}$, frequently from 300 to 5000 $h^{-1}$, i.e. in many cases from 500 to 3000 $h^{-1}$.

In a particularly elegant manner, a conventional inventive heterogeneously catalyzed dehydrogenation of at least one hydrocarbon to be dehydrogenated (e.g. propane) can be implemented in an inventive tray reaction chamber (both at dehydrogenation conversions of ≤30 mol % and >30 mol % (e.g. 40 mol %, or 50 mol %)).

Such an inventive tray reaction chamber comprises more than one catalyst bed catalyzing the dehydrogenation in spatial succession. The catalyst bed number may, for example, be from 1 to 20, appropriately from 2 to 8, but also from 3 to 6. The catalyst beds are preferably arranged in radial or axial succession. From an application point of view, it is appropriate to use the fixed catalyst bed type in such a tray reaction chamber.

In the simplest case, the fixed catalyst beds are arranged in the reaction chamber axially or in the annular gaps of concentric cylindrical grids. However, it is also possible to arrange the annular gaps in the reaction chamber in segments one above the other and to conduct the gas, after it has passed radially through one segment, into the next segment above it or below it.

Appropriately, the reaction gas (starting gas), on its way from one catalyst bed to the next catalyst bed, is subjected to intermediate heating in the tray reaction chamber, for example by passing it over heat exchanger ribs heated with hot gases or by passing it through pipes heated with hot combustion gases or heat exchanger plates heated with hot gases.

When the process according to the invention in the tray reaction chamber is otherwise operated adiabatically, it is sufficient for dehydrogenation conversions (e.g. propane conversion) of ≤30 mol %, especially when using the catalysts described in DE-A 199 37 107, especially those of the exemplary embodiments, to conduct the starting gas into the reaction chamber preheated to a temperature of 400 or 450 to 550° C. (preferably from 400 to 500° C.) and to keep it within this temperature range inside the tray reaction chamber. This means that the entire inventive dehydrogenation can thus be implemented, at least with fresh catalysts, at comparatively moderate temperatures, which is found to be particularly favorable for the lifetime of the fixed catalyst beds between two regenerations.

It is even more elegant to carry out a conventional heterogeneously catalyzed dehydrogenation in the inventive reaction chamber (as likewise already addressed) substantially autothermally, i.e. to carry out the intermediate heating outlined above by a direct route (autothermal method).

To this end, a limited amount of molecular oxygen can be added advantageously to the reaction gas on its way through the inventive reaction chamber, for example after it has flowed through the first catalyst bed and between the downstream catalyst beds. Depending on the dehydrogenation catalyst used, limited combustion of the hydrocarbons present in the reaction gas, any coke or coke-like compounds already deposited on the catalyst surface and/or of hydrogen which has been formed in the course of the conventional heterogeneously catalyzed dehydrogenation (for example of a propane dehydrogenation) and/or has been added to the reaction gas can thus be brought about (it may also be appropriate from an application point of view to insert catalyst beds in the tray reaction chamber which have been charged with catalyst which specifically (selectively) catalyzes the combustion of hydrogen (and/or of hydrocarbon) (useful such catalysts include, for example, those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in the tray reaction chamber in alternation to the beds comprising dehydrogenation catalyst)). The heat of reaction released thus allows (quasi-adiabatic reactor configuration), in a quasi-autothermal manner, a virtually isothermal (internal temperature control) operating mode of the heterogeneously catalyzed (e.g. propane) dehydrogenation. With increasing selection of the residence time of the reaction gas mixture in the catalyst bed, a (e.g. propane) dehydrogenation is thus possible at decreasing or substantially constant temperature, which enables particularly long lifetimes between two regenerations.

By virtue of subsequent combustion, carried out as described, of molecular hydrogen formed in the course of the dehydrogenation, a nonoxidative conventional heterogeneously catalyzed dehydrogenation becomes an oxidative conventional heterogeneously catalyzed dehydrogenation in the sense of the present application.

In general, oxygen feeding as described above should be undertaken such that the oxygen content of the reaction gas, based on the amount of hydrocarbon to be dehydrogenated and dehydrogenated hydrocarbon present therein (e.g. propane and propylene) is from 0.01 or 0.5 to 30% by volume. Useful oxygen sources are either pure molecular oxygen or oxygen diluted with inert gas, for example CO, $CO_2$, $N_2$, noble gases, but in particular also air. The resulting combustion gases generally have an additional diluting effect and thus promote the heterogeneously catalyzed (e.g. propane) dehydrogenation.

The isothermicity of a conventional heterogeneously catalyzed (e.g. propane) dehydrogenation can be improved further by incorporating closed (for example tubular) internals which have favorably, but not necessarily, been evacuated before filling in the spaces between the catalyst beds. Such internals may also be placed into the particular catalyst bed. These internals comprise suitable solids or liquids which evaporate or melt above a certain temperature and consume heat as they do so, and, when the temperature falls below this value, condense again and release heat as they do so.

Another means of heating the starting gas or the starting gas stream for a conventional heterogeneously catalyzed (e.g. propane) dehydrogenation in the inventive reaction chamber to the required reaction temperature is to combust a portion of the hydrocarbon to be dehydrogenated (e.g. of the propane) and/or $H_2$ present therein by means of the molecular oxygen present in the starting gas on entry into the reaction chamber (for example over suitable specific combustion catalysts, for example by simply passing it over and/or passing it through), and bringing about the heating to the reaction temperature desired (for the dehydrogenation) by means of the heat of combustion thus released. The resulting combustion products, such as $CO_2$, $H_2O$ and the $N_2$ which may accompany the molecular oxygen required for the combustion, are advantageous inert diluent gases.

The aforementioned hydrogen combustion can be implemented in a particularly elegant manner as described in WO 03/076370 or DE-A 102 11 275. In other words, in a process for continuous conventional oxidative heterogeneously catalyzed partial dehydrogenation of hydrocarbon to be dehydrogenated (e.g. in propane) in the inventive reaction chamber, in which at least one starting gas stream comprising at least one hydrocarbon to be dehydrogenated (e.g. propane), molecular oxygen, molecular hydrogen and, if appropriate, steam is fed continuously to the reaction chamber, in the reaction chamber, the at least one hydrocarbon to be dehydrogenated is conducted through at least one catalyst bed disposed in the reaction chamber, over which molecular hydrogen and, at least partially, at least one dehydrogenated hydrocarbon (e.g. propylene) are formed by conventional heterogeneously catalyzed dehydrogenation, further gas comprising molecular oxygen is added if appropriate to the reaction gas on its way through the reaction chamber after it has entered the inventive reaction chamber, the molecular oxygen in the molecular hydrogen present in the reaction gas in the reaction chamber is oxidized at least partly to steam, and at least one product gas stream which comprises molecular hydrogen, steam, dehydrogenated hydrocarbon (e.g. propylene) and hydrocarbon to be dehydrogenated (e.g. propane) is withdrawn continuously from the reaction chamber, wherein the at least one product gas stream withdrawn from the inventive reaction chamber is divided into two portions of identical composition and one of the two portions is recycled as dehydrogenation cycle gas into the at least one starting gas stream fed to the inventive reaction chamber, and the other portion is used further in another way (for example for the purpose of a heterogeneously catalyzed partial oxidation of dehydrogenated hydrocarbon formed in the reaction chamber).

For example, the product gas of an inventive, oxidative or nonoxidative heterogeneously catalyzed dehydrogenation of propane to propylene may have the following contents from 25 to 60% by volume of propane,
from 8 to 25% by volume of propylene,
from ≥0 to 25% by volume of $H_2$ and
from ≥0 to 30% by volume of $CO_2$.

In the above remarks, propane has always been mentioned in individualized form as the hydrocarbon to be dehydrogenated under heterogeneous catalysis in a conventional, nonoxidative or oxidative manner. Of course, the procedures described can also be applied to all other compounds listed as hydrocarbons to be dehydrogenated at the outset of this document. In particular, mention should be made among these once again of butane (to butene and/or butadiene; especially isobutane to isobutene) and of butenes to butadiene.

Quite generally, the at least one starting gas stream of an inventive, oxidative or non-oxidative heterogeneously catalyzed dehydrogenation generally comprises ≥5% by volume of the hydrocarbon to be dehydrogenated (e.g. propane). In addition, it may comprise, for example:

a) $N_2$ and $H_2O$;
b) $N_2$, $O_2$ and $H_2O$;
c) $N_2$, $O_2$, $H_2O$ and $H_2$;
d) $N_2$, $O_2$, H2O, $H_2$ and $CO_2$.

As already mentioned, the process according to the invention will in many cases be followed by a process for heterogeneously catalyzed partial oxidation of dehydrogenated hydrocarbon obtained (for example propylene to acrolein and/or acrylic acid), preferably accompanied by unconverted hydrocarbon to be dehydrogenated (e.g. propane) as an inert gas. The product gas stream withdrawn (continuously) from the inventive reaction chamber will be used as such or after removal of at least a portion of its constituents (e.g. $H_2$, $H_2O$, $N_2$, etc.) other than the dehydrogenated hydrocarbon (e.g. propylene) and the (unconverted) hydrocarbon to be dehydrogenated (e.g. propane) to charge at least one oxidation reactor, and the dehydrogenated hydrocarbon present in the charge gas mixture (e.g. propylene) will be subjected to a selective heterogeneously catalyzed partial gas phase oxidation with molecular oxygen to give a product gas mixture B comprising (partial oxidation product) target product (for example acrolein or acrylic acid or a mixture thereof), and also generally unconverted hydrocarbon to be dehydrogenated (e.g. propane), excess molecular oxygen and, if appropriate, unconverted hydrocarbon to be dehydrogenated (e.g. propylene).

In a downstream separation zone B, target product (for example acrolein or acrylic acid or a mixture thereof) present in product gas mixture B will be removed and, from the remaining residual gas comprising unconverted hydrocarbon to be dehydrogenated (e.g. propane), molecular oxygen and, if appropriate, unconverted dehydrogenated hydrocarbon (e.g. propylene), at least a portion comprising unconverted hydrocarbon to be dehydrogenated (e.g. propane) and, if appropriate, unconverted molecular oxygen and, if appropriate, unconverted dehydrogenated hydrocarbon (e.g. propylene) will be recycled into the process according to the invention as partial oxidation cycle gas (for example as a constituent of the starting gas stream).

When the process according to the invention (but also otherwise) is, for example, an oxidative conventional heterogeneously catalyzed partial dehydrogenation of propane to propylene, and the partial oxidation which follows is that of propylene to acrolein or to acrylic acid or to a mixture thereof, the at least one starting gas stream fed to the inventive reaction chamber may comprise, for example, as significant contents:

from ≥0 to 20 or to 10, frequently from 0 to 6% by volume of propylene,
from ≥0 to 1, in many cases from 0 to 0.5, frequently from 0 to 0.25% by volume of acrolein,
from ≥0 to 0.25, in many cases from 0 to 0.05, frequently from 0 to 0.03% by volume of acrylic acid,
from ≥0 to 20 or to 5, in many cases from 0 to 3, frequently from 0 to 2% by volume of $CO_x$,
from 5 to 50, preferably from 10 to 20% by volume of propane,
from 20 or 30 to 80, preferably from 50 to 70% by volume of nitrogen,
from ≥0 to 5, preferably from 1.0 to 2.0% by volume of oxygen,
from ≥0 to 20, preferably from 5.0 to 10.0% by volume of $H_2O$, and
from ≥0, frequently from ≥0.01, often from ≥0.05 to 10, preferably from 1 to 5% by volume of $H_2$.

Acetic acid may also be present in small amounts (approximately comparable to the possible acrylic acid contents).

Typically, target product (for example acrylic acid) is removed from product gas mixture B by converting the target product (for example the acrylic acid) into the condensed phase. This can be done by absorptive and/or condensative (cooling) measures. Useful absorbents in the case of acrylic acid as the target product are, for example, water, aqueous solutions or high-boiling ($T_{boil} > T_{boil}$ of acrylic acid at 1 atm), especially hydrophobic, organic solvents. More preferably, the conversion into the condensed phase in the case of acrylic acid is effected by fractional condensation of product gas mixture B. Preference is given to effecting the absorptive and/or condensative conversion of acrylic acid from product gas mixture B into the condensative phase in columns comprising separating internals, in which the product gas mixture is normally conducted ascending from the bottom upward. The absorbent is generally introduced at the top of the column, at which the residual gas is normally released from the column.

The further removal of the acrylic acid from the condensed phase is effected generally in the desired purity using at least one thermal separation process. This is understood to mean those processes in which two different substance phases (for example liquid/liquid; gaseous/liquid; solid/liquid; gaseous/solid, etc.) are obtained and contacted with one another. Owing to the inequilibrium existing between the phases, heat and mass transfer takes place between them and ultimately causes the desired separation (removal). The term "thermal separation process" reflects that it requires either the withdrawal or the supply of heat to obtain the formation of the substance phases and/or that the withdrawal or the supply of thermal energy promotes or maintains the mass transfer.

Preferably in accordance with the invention, the at least one thermal separation process comprises at least one crystallizative removal from liquid phase. Appropriately in accordance with the invention, the at least one crystallizative removal of acrylic acid is a suspension crystallization, and the suspension crystals are advantageously washed with molten crystals which have been removed beforehand and washed in a wash column (a gravimetric, or a mechanical, or a hydraulic wash column; preference is given in accordance with the invention to the latter). Otherwise, useful thermal separation processes are, for example, extractive, desorptive, cristallizative, rectificative, azeotropically distillative, azeotropically rectificative, distillative and/or stripping processes. In general, pure acrylic acid will be obtained by employing combinations of different thermal separation processes of those mentioned.

The removal of acrylic acid described can be followed by a process for free-radical polymerization (especially for preparing water-superabsorbent polyacrylic acids and/or their partly or fully neutralized alkali metal (preferably Na) salts), in which acrylic acid removed is polymerized free-radically to prepare polymers.

It is also possible for the removal of acrylic acid described to be followed by a process for preparing acrylic esters, in which removed acrylic acid is esterified with alcohols (preferably alkanols, more preferably $C_1$- to $C_{12}$-alkanols) (generally under acid catalysis).

The process for esterification may in turn be followed by a process for free-radical polymerization, in which acrylic ester thus prepared is polymerized.

Disregarding the inventive peculiarity of the inventive reaction chamber, processes according to the invention for preparing propylene from propane as the propylene source for partial oxidations thereof to prepare acrolein and/or acrylic acid are known, including a cycle gas method of oxidation cycle gas and, if appropriate, dehydrogenation cycle gas. For example, descriptions of such multistage processes can be found in the documents DE-A 10 2005 022 798, DE-A 102 46 119, DE-A 102 45 585, DE-A 10 2005 049 699, DE-A 10 2004 032 129, DE-A 10 2005 013 039, DE-A 10 2005 010 111, DE-A 10 2005 009 891, DE-A 102 11 275, EP-A 117 146, U.S. Pat. No. 3,161,670, DE-A 33 13 573, WO 01/96270, DE-A 103 16 039, DE-A 10 2005 009 885, DE-A 10 2005 052 923, DE-A 10 2005 057 197, WO 03/076370, DE-A 102 45 585, DE-A 22 13 573, U.S. Pat. No. 3,161,670 and the prior art cited in these documents. DE-A 102 19 686 discloses the corresponding procedure in the case of preparation of methacrolein and/or methacrylic acid.

Detailed descriptions of absorptive and/oder condensative processes for converting acrylic acid from a product gas mixture B into the condensed phase can likewise be found in the prior art. This includes the documents DE-A 103 36 386, DE-A 196 31 645, DE-A 195 01 325, EP-A 982 289, DE-A 198 38 845, WO 02/076917, EP-A 695 736, EP-A 778 225, EP-A 1 041 062, EP-A 982 287, EP-A 982 288, US-A 2004/0242826, EP-A 792 867, EP-A 784 046, EP-A 695 736 (especially absorptive) and WO 04/035514, DE-A 199 24 532, DE-A 198 14 387, DE-A 197 40 253, DE-A 197 40 252 and DE-A 196 27 847 (especially condensative).

In addition, descriptions of such absorptive and/or condensative removals of acrylic acid from product gas mixtures B can also be found in the documents EP-A 1 338 533, EP-A 1 388 532, DE-A 102 35 847, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 195 01 325, DE-A 102 47 240, DE-A 197 40 253, EP-A 695 736, EP-A 1 041 062, EP-A 117 146, DE-A 43 08 087, DE-A 43 35 172, DE-A 44 36 243, DE-A 103 32 758 and DE-A 199 24 533. In principle, however, it is also possible to proceed as described in DE-A 103 36 386, DE-A 101 15 277, DE-A 196 06 877, EP-A 920 408, EP-A 1 068 174, EP-A 1 066 239, EP-A 1 066 240, WO 00/53560, WO 00/53561, DE-A 100 53 086, WO 01/96271, DE-A 10 2004 032 129, WO 04/063138, WO 04/35514, DE-A 102 43 625 and DE-A 102 35 847.

When the hydrocarbon to be dehydrogenated for the process according to the invention is propane, it will preferably be fed to the at least one starting gas stream as crude propane in accordance with the teaching of DE-A 102 45 585.

Generally, the at least one starting gas stream will comprise hydrocarbon to be dehydrogenated at least to an extent of 5% by volume. Frequently, this proportion by volume will be at values of on a corresponding basis of ≥10% by volume, often ≥15% by volume and usually ≥20% by volume or ≥25% by volume, or ≥30% by volume. In general, this proportion by volume, however, will be at values on the same basis of ≤90% by volume, usually ≤80% by volume and often ≤70% by volume. The above data apply especially in the case of propane as the hydrocarbon to be dehydrogenated and propylene as the dehydrogenated hydrocarbon. Of course, they also apply where isobutane is the hydrocarbon to be dehydrogenated and isobutene is the dehydrogenated hydrocarbon.

Remarkably, for the performance of an inventive conventional (oxidative or nonoxidative) heterogeneously catalyzed dehydrogenation, especially for an adiabatic operating mode, the interior of a simple shaft furnace ("shaft furnace reactor") is sufficient as the at least one inventive reaction chamber which comprises at least one catalyst bed (for example the at least one fixed catalyst bed) and is flowed through axially and/or radially by the starting gas stream.

In the simplest case, it is, for example, a substantially cylindrical vessel whose internal diameter is from 0.1 to 10 m, possibly from 0.5 to 5 m, and in which the at least one fixed catalyst bed is placed on a support device (for example a grid). The reaction chamber charged with catalyst, whose inventive shell is thermally insulated in adiabatic operation, is appropriately flowed through axially with the hot starting gas stream comprising the hydrocarbon to be dehydrogenated (e.g. the propane). The catalyst geometry may be either spherical or annular or strand-shaped. Since the reaction chamber in the case just described can be implemented by a very inexpensive apparatus, all catalyst geometries which have a particularly low pressure drop are preferable. These are in particular catalyst geometries which lead to a large cavity volume or are structured, for example monoliths or honeycombs. To implement radial flow of the reaction gas comprising the hydrocarbon to be dehydrogenated (e.g. the propane), the inventive reaction temperature may, for example, comprise two concentric cylindrical grids and the catalyst bed may be disposed in their annular gap. In the adiabatic case, the shell surrounding it (the jacket) would, if appropriate, in turn be thermally insulated. In the case of a substantially cylindrical shaft furnace flowed through axially, it is advantageous for the process according to the invention in the case of an adiabatic operating mode when the dimension A of the reaction chamber at right angles to the cylindrical axis is at least 5 times, preferably at least 10 times and more preferably at least 15 times the bed height S of the at least one catalyst bed in axial direction. In general, the aforementioned ratio of A:S will, however, be ≤200, typically ≤150 and usually ≤100.

Against the background of the statements above, the present invention comprises, as part of the inventive subject matter, especially a (material) shell E which encloses an interior I (the reaction chamber) and has at least one first orifice O1 for feeding at least one gas stream (material stream) S into the interior I and at least one second orifice O2 for removal A (withdrawal) of a gas stream (material stream) S fed to the interior I beforehand via the at least one first orifice O1 from the interior I, the surface of the shell E, on its side in contact with the interior I, being manufactured at least partly, in a layer thickness d of at least 1 mm, from a steel S which has the following elemental composition:

- from 18 to 30% by weight of Cr,
- from 9 to 36% by weight of Ni,
- from 1 to 3% by weight of Si,
- from 0.1 to 0.3% by weight of N,
- from ≥0 to 0.15% by weight of C,
- from ≥0 to 4% by weight of Mn,
- from ≥0 to 4% by weight of Al,
- from ≥0 to 0.05% by weight of P,
- from ≥0 to 0.05% by weight of S, and
- from ≥0 to 0.1% by weight of one or more rare earth metals, and, apart from these, Fe and impurities resulting from production, the percentages each being based on the total weight.

Advantageously, the total amount of the impurities resulting from the production, quite generally and on the same basis, is ≤1% by weight, preferably ≤0.75% by weight, more preferably ≤0.5% by weight and most preferably ≤0.25% by weight. In general, the total amount of the impurities resulting from the production in the steel will, however, be ≥0.1% by weight. The rare earth metal preferred in accordance with the invention is Ce. Preferably in accordance with the invention, the relevant steel therefore comprises from ≥0 to 0.1% by weight of Ce or Ce and of one or more rare earth metals other than Ce. The interior I of all shells E, after the introduction of at least one catalyst bed comprising dehydrogenation catalyst, is suitable for performing processes according to the invention (especially those for adiabatic heterogeneously catalyzed conventional nonoxidative or oxidative dehydrogenation of propane to propylene).

Advantageously in accordance with the invention, the surface of the shell E, on its side in contact with the interior I, is manufactured from the relevant steel S, in a layer thickness d of at least 1 mm, to an extent of at least 10%, preferably to an extent of at least 20%, or to an extent of at least 30%, even more preferably to an extent of at least 40%, or to an extent of at least 50%, even more advantageously to an extent of at least 60%, or to an extent of at least 70%, better to an extent of at least 80% or to an extent of at least 90% and at best to an extent of at least 95% or to an extent of at least 100% of its total surface area.

Advantageously in accordance with the invention, the aforementioned d is at least 2 mm, or at least 3 mm, or at least 4 mm, or at least 5 mm. It will be appreciated that d may also be from ≥5 mm to 30 mm, or up to 25 mm, or up to 20 mm, or up to 15 mm, or up to 10 mm. Most preferably, the shell E is manufactured from an inventive steel S in its entirety or to an extent of at least 80% of its weight, better to an extent of at least 90% or to an extent of at least 95% of its weight.

Advantageously, the capacity of the interior I (calculated empty) is from 5 m³ to 500 m³, often from 10 m³ to 400 m³, frequently from 20 m³ to 300 m³, in many cases from 30 m³ to 200 m³, or from 50 m³ to 150 m³.

Of course, useful steels for the steel S of the shell E are also all other inventive steels S already mentioned in this document, and in the classification of preference already given above in this document. Advantageously, the steel S has been alonized, alitized and/or aluminized on its side in contact with the interior I.

In particular, the present invention relates to shells E whose interior I comprises at least one catalyst suitable for a heterogeneously catalyzed partial dehydrogenation of a hydrocarbon to be dehydrogenated (dehydrogenation catalyst). Useful such catalysts are in particular all dehydrogenation catalysts detailed in this document.

The amount of catalyst present in the interior of the shell E may be from 100 kg to 500 t (metric tons) or from 200 kg to 400 t, or from 300 kg to 300 t, or from 400 kg to 200 t, or from 500 kg to 150 t, or from 1 t to 100 t, or from 10 t to 80 t, or from 20 t to 60 t. In this context, any inert shaped bodies which exclusively dilute the catalysts are not counted.

The present invention further relates to shells E whose interior I comprises at least one grid (preferably at least two concentric grids). Advantageously, the shell E has (comprises) an annular (hollow cylindrical) segment R (or such a section) (in which case the ring interior $I_R$ forms part of the interior I).

If D is half of the difference between the external diameter A (calculated without outer thermal insulation) and the internal diameter of the annular segment R, the ratio $V_1$ of D to A is, preferably in accordance with the invention, from 1:10 to 1:1000, in many cases from 1:20 to 1:800, often from 1:30 to 1:600, in many cases from 1:40 to 1:500, or from 1:50 to 1:400, or from 1:60 to 1:300, but in many cases also from 1:70 to 1:200, or from 1:80 to 1:150.

The ratio $V_2$ of the height H (the separation of the two parallel circular planes delimiting the annular segment R) and A ($V_2$=H:A) may be either >1, or =1, or <1.

When $V_2$>1, it is typically from 2 to 10, frequently from 4 to 8 and often 6. When $V_2$<1, it is typically from 0.01 to 0.95, frequently from 0.02 to 0.9, often from 0.03 to 0.8, in many cases from 0.05 to 0.7, or from 0.07 to 0.5 or from 0.1 to 0,4. Possible values for $V_2$ are thus also 0.2 and 0.3.

When $V_2$>1, A is usually from ≥0.5 m to 5 m, frequently from 1 m to 4 m, and appropriately from 2 m to 3 m.

When $V_2$<1, A is typically from ≥0.5 m to 8 m, preferably from 2 m to 6 or 7 m and often from 2.5 m to 5 m.

When $V_2$=1, typical external diameters A are from 0.5 to 8 m, or from 2 to 6 or 7 m, or from 2.5 m to 5 m.

When $V_2$>1, the annular interior (the ring interior) of the annular segment R of the shell E is especially suitable for the configuration of an inventive tray reaction chamber which is flowed through radially and is particularly suitable for the process according to the invention. To this end, the annular interior $I_R$ appropriately comprises fixed catalyst beds introduced between the annular gaps of concentric grids, the annular gap advantageously being arranged in sections one on top of another such that a reaction gas flowing through it, after radial passage in one section, is conducted into the next section above it or below it. The number of aforementioned catalyst beds may be from 1 to 20, appropriately from 2 to 8 and preferably from 3 to 6. In other words, preference is given in accordance with the invention to shells E with a ring interior $I_R$ which have annular gaps which are arranged one on top of another in sections and consist of grids concentric in each case and whose $V_2>1$.

When $V_2<1$, the annular interior (the ring interior) of the annular segment R of the shells E is especially suitable for the configuration of an inventive tray reaction chamber which is flowed through axially and is particularly suitable for the process according to the invention. To this end, the annular interior $I_R$ appropriately comprises catalyst beds introduced onto grids arranged in axial succession (i.e. along the ring axis or cylinder axis), which are flowed through in succession by the reaction gas. The number of aforementioned catalyst beds may be from 1 to 20, appropriately from 2 to 8 and preferably from 3 to 6. In general, they are arranged equidistantly.

In other words, preference is given in accordance with the invention to shells E having a ring interior $I_R$ which comprise grids arranged in axial succession and whose $V_2<1$. The latter is true especially when H is from 2 m to 4 m (preferably from 3 to 4 m, or 3.50 m) and the internal diameter of the annular segment R (at a wall thickness of from 1 to 4 cm) is from 5.90 m to 6.30 m. Appropriately, the number of catalyst bed trays arranged in axial succession in the aforementioned case is three. The bed height of a catalyst bed (for example of the catalyst according to Ex. 4 of DE-A 10219879) will appropriately be from 10 to 60 cm (e.g. 30 cm).

Appropriately from an application point of view, the two parallel circular planes delimiting the annular segment R are concluded by a hood in each case (supplemented to make shell E). In principle, the hoods may have the form of a flat base (lid) or else be curved. Preference is given in accordance with the invention to hoods curved on both sides of the annular segment R. It is possible for the curvature to have torispherical shape according to DIN 28013 or semiellipsoidal shape according to DIN 28011. The curve of the lower hood will normally point away from the interior $I_R$ (be curved outward, convex). The curvature of the upper hood may be either concave or convex relative to the interior $I_R$. In a simple manner from an application point of view, both hoods are curved convex relative to the interior $I_R$. In this case, the at least one first orifice O1 is appropriately in the center of the upper hood and the at least one second orifice O2 is appropriately in the center of the lower hood. The orifices O1 and O2 are preferably circular. Appropriately from an application point of view, their cross sections are selected such that their ratio corresponds to the ratio of the contemplated volume streams flowing in and out through them. At a height H of from 2 m to 4 m (preferably from 3 to 4 m, or 3,50 m) and an internal diameter of the annular segment of from 5.90 to 6.30 m, the diameter of the at least one first orifice O1 may, for example, typically be 1200 mm and the diameter of the at least one second orifice, O2, for example, typically 1400 mm. Advantageously from an application point of view, the wall thickness of the lower hood is thicker than D of the annular segment R. In this case, the part of the hood wall protruding beyond D may bear the grids (and catalyst beds) arranged, for example, in axial succession (stacked on top of another) in the annular segment R.

However, the individual annular grids may also be composed of (assembled from) uniform (separate) circle sectors (grid sectors) (like the cross section of a slice of orange). From an application point of view, preference is given to twelfth, or eighth, or sixth, or quarter, or third circle sectors. The grid circle sectors may in turn rest on open framework circle sectors. The lowermost framework circle sectors may, adjusted to the curvature of the lower hood, be continued and placed into the convex curvature of the lower hood as the element bearing the framework circle sectors. The framework circle sectors of grid sectors disposed above them may then in each case be placed onto those of the catalyst tray disposed immediately below them.

In principle, shells E may be manufactured seamlessly from the annular segment R and the two hoods concluding it. However, the segment R and the hoods are generally manufactured separately and subsequently have to be bonded to one another in a very substantially gas-tight manner (gas leakage $<10^{-4}$ mbar·l/s). In the case of the lower hood, this bonding with the annular segment R is preferably effected by welding it on. In the case of the upper hood, however, the bonding with the annular segment R is advantageously undertaken by flanging it on (the removability of the upper hood eases the filling with and the withdrawal of catalyst, for example in the case of a partial catalyst change or in the case of a full catalyst change). Particular preference is given to a flange bond with weld lip sealing (preferably in accordance with the invention, the latter will be manufactured preferably from steel sheets of a steel S which have a thickness of approx. 2 mm).

Preferably in accordance with the invention, the shaped catalyst bodies will not be placed directly onto the grids. This is because the shaped catalyst bodies typically have a smaller dimension than the mesh width of the grid. Appropriately, therefore, a layer (height: from 1 to 10 cm, preferably from 5 to 10 cm) of steatite spheres of diameter from 3 to 10 cm, frequently from 4 or 5 to 8 cm, is placed first onto a grid (preference is given to using steatite C220 from CeramTec). In principle, also useful are shaped bodies other than spheres (for example cylinders or rings) which have a longest dimension (longest direct line connecting two points on their surface) corresponding to the aforementioned diameters. Useful alternative inert materials to steatite include in particular aluminum oxides, silicon dioxide, thorium dioxide, zirconium dioxide, silicon carbide or silicates such as magnesium silicate and aluminum silicate. Only to this inert layer is the catalyst bed then applied. The reaction gas flows through the reaction chamber in a corresponding manner from the top downward. At the top, the catalyst bed is covered once again by an appropriate inert bed.

A pipeline feeding the at least one starting gas stream is normally bonded to the at least one first orifice O1 by flanging it on, as is the pipeline removing the at least one product gas stream to the at least one second orifice O2.

For proper and safe operation, the aforementioned (pipe) lines are preferably equipped with devices for compensating longitudinal expansion effects, as can occur, for example, owing to temperature changes, and it is advantageous to use compensators which feature a lateral mode of action.

These compensators which generally have a multilayer design may be manufactured from the same material as the pipeline itself. However, particularly advantageous embodiments are those with (generally: gas-permeable rigid inner tube and gas-impermeable elastic outer sleeve (gas-impermeable elastic outer tube)) an inner tube part, preferably manufactured from an inventive steel S, which is in contact with the gas to be conducted and appropriately has a gas-permeable expansion joint and an external, gas-impermeable, elastic, corrugated part which is manufactured at least partly from an especially mechanically and thermally stressable material, for example material 1.4876 (designation according to VdTÜV-Wb 434) or 1.4958/1.4959 (designation according to DIN 17459) or INCOLOY® 800 H or 800 HT, or nickel-base material 2.4816 (alternative designation Alloy 600) or 2.4851 (alternative designation Alloy 601).

In order to minimize the residence time of a gas fed in the interior I of a shell E in a manner advantageous in accordance with the invention, it is appropriate to reduce the inner hood volume by means of displacer bodies mounted within the hood.

Alternatively to the aforementioned approach to a solution, it is advisable to use a concave (into the interior of the annular segment R) curved hood. In this case, the at least one orifice O1 for feeding the at least one gas stream into the interior will advantageously not be mounted in the center of the upper hood. Instead, it is appropriate in this case, appropriately distributed uniformly around the circumference of the uppermost section of the annular segment R, to mount windows with passage to the annular interior $I_R$ as such orifices. From the outside, a ring channel which is attached to the window bar in a gas-tight manner (similarly to the ring channel for feeding salt melt in a salt bath-cooled tube bundle reactor; cf. number 22 in DE-A 19806810, FIG. 1) will appropriately be mounted around the window bar. The starting gas stream will then be conducted to the ring channel which distributes this gas stream uniformly over all windows and feeds it to the interior $I_R$ through the windows. In the interior $I_R$, impingement plates may be mounted at controlled distance from the windows and additionally uniformize the distribution of the starting gas stream fed to the interior $I_R$ over the cross section of the interior $I_R$.

For the purpose of adiabatic performance of a heterogeneously catalyzed dehydrogenation of at least one hydrocarbon to be dehydrogenated in the interior I (especially in the interior $I_R$) of the shell E, thermal insulation material (=materials which reduce the heat transfer number for the heat transfer from the shell to the environment) will be mounted on the side of the shell E (including hoods and feed and removal lines) facing away from the interior I (for example glass wool, rockwool and/or ceramic wool). If required, the aforementioned insulation materials may additionally be applied to the side of the shell E facing toward the interior. In this case, they may themselves have a separating envelope, for example of inventive steel sheet. Overall, the thermal insulation is preferably such that, based on single pass of the reaction gas to the interior I, ≤10%, preferably ≤5% and more preferably ≤2% of the heat content averaged over the interior I flows out to the external environment of the shell E during the performance of a process according to the invention in the interior I. For the case of an adiabatic conventional oxidative heterogeneously catalyzed dehydrogenation of at least one hydrocarbon to be dehydrogenated (e.g. propane to propylene), lines will be conducted through the shell E into the interior I, through which, for example, gas comprising molecular oxygen (e.g. air) which serves for exothermic catalytic combustion of molecular hydrogen and, if appropriate, hydrocarbon may be injected between the catalyst trays.

As an alternative embodiment, useful shells E for the process according to the invention are also those which describe a hollow sphere. In these cases, the shell E has a hollow spherical zone segment K, which can be imagined as a hollow sphere intersected by two parallel planes. Between the two planes, the hollow spherical zone segment K is then formed and, above and below the two planes, a hollow spherical cap which can assume the function of the hoods outwardly concluding the segment K is cut off in each case. The interior $I_K$ of the segment K is in turn formed by the particularly relevant part of the interior I (corresponding to $I_R$). Otherwise, in the case of a spherical shell E too, everything stated for the cylindrical shell E with regard to the accommodation of catalyst trays and feed and removal orifices O1 and O2 applies analogously The same applies to the statements on thermal insulation. Around the shell E itself, a support ring will generally advantageously be mounted, which, appropriately placed on four supports, holds the shell E.

When the interior I formed by the shell E comprises internals such as grids, etc., they are preferably likewise manufactured from inventive steel S. However, they may also be manufactured for the process according to the invention, for example, from fired clays (aluminum silicates) or steatite (for example C 220 from CeramTec), or other (essentially inert) high-temperature ceramic materials such as aluminum oxides, silicon dioxide, thorium dioxide, zirconium dioxide, silicon carbide or other silicates such as magnesium silicate.

Advantageously in accordance with the invention, the surface of the shell E has been manufactured from inventive steel S in a layer thickness d of at least 1 mm (or at least 2 mm, or at least 3 mm, or at least 4 mm, or at least 5 mm, or from ≥5 mm to 30 mm, or up to 25 mm, or up to 20 mm, or up to 15 mm, or up to 10 mm) at least on its part-surface in contact with the interior $I_R$ or the interior $I_K$ (or on at least 10%, or at least 20%, or at least 30%, or at least 40%, or at least 50%, or at least 60%, or at least 70%, or at least 80%, or at least 90% or at least 95% of this part-surface). The segment R or the segment K of the shell E has advantageously been manufactured from inventive steel S to an extent of at least 80%, or to an extent of at least 90%, advantageously to an extent of at least 95% and most advantageously to an extent of 100% of its weight. The statements made for the segments R and K also relate thus to the hoods and their inner surfaces.

When a shell E is manufactured by welding inventive steel S, such welding is preferably effected in accordance with the invention with identical materials, i.e. base material and additional welding material are identical. In principle, it is also possible for this purpose to use lower-melting steel whose elemental composition approximates very closely to inventive steel S. Preference is given to effecting the welding under inert gas atmosphere (more preferably under argon and/or helium).

Suitable fusion welding processes are light arc welding with rod electrodes and also protective gas welding (in particular by the WIG method). The protective gas used is preferably a nitrogen-containing protective gas. The welding electrodes used may be the welding rods Thermanit D (W 22 12 H) or Thermanit C (W 25 20 Mn) or Sandvik 22 12 HT.

Finally, it should also be noted that the inventive steels S, even with regard to their comparatively restricted catalyzing action, are satisfactory with regard to a full combustion of hydrocarbon to be dehydrogenated and/or dehydrogenated hydrocarbon in the presence of molecular oxygen.

EXAMPLES AND COMPARATIVE EXAMPLES

I. General Experimental Description

1. Configuration of the reaction tubes

The geometry of the reaction tubes was: length 0.55 m external diameter (A) from 21.34 to 22 mm wall thickness (W) from 2 to 2.77 mm Over its entire length, the particular reaction tube was filled with inert spheres made of steatite C 220 from CeramTec. The sphere diameter was from 1.5 mm to 2.5 mm with substantially uniform distribution.

2. The material used for the reaction tube was 5 different materials.
Material 1 (M1): stainless steel of DIN materials number 1.4841 (A=22 mm, W=2 mm),
Material 2 (M2): stainless steel of DIN materials number 1.4541 which had the following elemental composition (A=22 mm, W=2 mm):
 17.31% by weight of Cr,
 10.05% by weight of Ni,
 0.51% by weight of Si,
 0.017% by weight of N,
 0.042% by weight of C,
 1.17% by weight of Mn,
 0.025% by weight of P,
 <0.0005% by weight of S,
 0.29% by weight of Ti and, apart from these, Fe and impurities resulting from production, the percentages each being based on the total weight (test certificate from Sterling Tubes).
Material 3 (M3): stainless steel of DIN materials number 1.4541, but surface-alonized on its side facing the reaction chamber (A=22 mm, W=2 mm).
Material 4 (M4): fired aluminum nitride (A=22 mm, W=2 mm)
Material 5 (M5): inventive stainless steel of the following elemental composition (A=21.34 mm, W=2.77 mm):
 20.87% by weight of Cr,
 10.78% by weight of Ni,
 1.54% by weight of Si,
 0.161% by weight of N,
 0.082% by weight of C,
 0.75% by weight of Mn,
 0.02% by weight of P,
 0.0026% by weight of S,
 0.05% by weight of Ce, and
 apart from these, Fe and impurities resulting from production, the percentages each being based on the total weight.
3. The different reaction tubes were charged with the following starting gas streams, as are typical in their composition for an inventive heterogeneously catalyzed dehydrogenation of propane to propylene:
Feed A: 31.7% by volume of propane,
 51.0% by volume of $N_2$,
 3.09% by volume of $O_2$,
 6.33% by volume of $H_2$, and
 7.88% by volume of $H_2O$
Feed B: 33.8% by volume of propane,
 54.5% by volume of $N_2$,
 3.3% by volume of $O_2$, and
 8.4% by volume of $H_2O$.
Feed C: 33.8% by volume of propane,
 57.8% by volume of $N_2$, and
 8.4% by volume of $H_2O$.
The selected propane loading of the fixed bed of inert steatite spheres was selected to 20 l (STP)/l·h in all cases.
4. The reaction tube was in each case mounted in a radiative oven (electrically heated ceramic body with hollow cylindrical guide for accommodating the reaction tube with a gap width of 0.2 cm to the reaction tube outer wall).
5. The particular reaction tube was flowed through as described by the particular starting gas stream (this had an inlet temperature of 200° C. in each case). At the same time, the temperature $T^A$ of the outer wall of the reaction tube was increased such that the maximum temperature $T^M$ in the reaction tube increased from 400° C. to 700° C. with a gradient of 10° C./h in a substantially linear manner (this simulates the compensation of a catalyst bed being deactivated in continuous operation by increasing the reaction temperature).

Subsequently, the regeneration of a dehydrogenation catalyst bed was simulated. To this end, the reaction tube was flowed through first with 420 ml (STP)/min of $N_2$ of inlet temperature 200° C. while the temperature $T^M$ was kept at 700° C.

While retaining the temperature $T^M=700$° C., the following gas flow-through program was run through:
 over 60 min, lean air (mixture of air (85.4 ml (STP)/min) and $N_2$ (341.6 ml (STP)/min));
 then—over 60 min, 417 ml (STP)/min of air;
 then—over 15 min, 417 ml (STP)/min of $N_2$;
 then—over 60 min, 168 ml (STP)/min of $H_2$.

The particular reaction tube, flowed through by the particular feed, was then brought from $T^M=700$° C. to $T^M=400$° C. in a substantially linear manner with a $T^M$ gradient of 10° C./h.

Depending on the feed used and on the material used for the reaction tube, the following values $N^P$ (%) were determined at the temperatures $T^A$ of 500° C., 600° C., 650° C. and 700° C. (at the start of the reaction tube, the composition of the gas stream leaving was analyzed continuously (by gas chromatography); the total amount of by-product $N^P$ of the hydrocarbons other than propane (methane, ethane and ethylene), expressed as the total carbon content of this total amount of hydrocarbon by-product, based on the total amount of carbon fed to the reaction tube as propane (in %) was determined):

| Feed A | | | | | |
| --- | --- | --- | --- | --- | --- |
|  | M1 | M2 | M3 | M4 | M5 |
| 550° C. | 0.031 | 0.029 | 0.023 | 0.013 | 0.026 |
| 600° C. | 0.117 | 0.037 | 0.036 | 0.026 | 0.066 |
| 650° C. | 0.939 | 0.683 | 0.539 | 0.197 | 0.243 |
| 700° C. | 7.320 | 2.840 | 4.841 | 2.010 | 1.520 |

| Feed B | | | | | |
| --- | --- | --- | --- | --- | --- |
|  | M1 | M2 | M3 | M4 | M5 |
| 550° C. | 0.033 | 0.010 | 0.006 | 0.003 | 0.052 |
| 600° C. | 0.149 | 0.177 | 0.023 | 0.009 | 0.076 |
| 650° C. | 0.865 | 0.732 | 0.257 | 0.089 | 0.235 |
| 700° C. | 4.735 | 2.650 | 3.201 | 1.273 | 1.345 |

| Feed C | | | | | |
| --- | --- | --- | --- | --- | --- |
|  | M1 | M2 | M3 | M4 | M5 |
| 550° C. | 0.026 | 0.022 | 0.011 | 0.023 | 0.007 |
| 600° C. | 0.176 | 0.344 | 0.116 | 0.052 | 0.062 |
| 650° C. | 1.540 | 1.240 | 0.981 | 0.427 | 0.555 |
| 700° C. | 6.190 | 3.190 | 4.681 | 2.650 | 3.147 |

U.S. Provisional Patent Application No. 60/751,973 filed on 21 Dec. 2005, is incorporated into the present patent application by literature reference.

With regard to the abovementioned teachings, numerous changes to and deviations from the present invention are possible.

It can therefore be assumed that the invention, within the scope of the appended claims, can be performed differently from the way described specifically herein.

What is claimed is:

1. A shell E which encloses an interior I and has at least one first orifice O1 for feeding at least one gas stream into the interior I and at least one second orifice O2 for withdrawing a gas stream fed to the interior I beforehand via the at least one first orifice O1 from the interior I, the surface of the shell E, on its side in contact with the interior I, being manufactured at least partly, in a layer thickness d of at least 1 mm, from a steel S which has the following elemental composition:
   from 18 to 30% by weight of Cr,
   from 9 to 36% by weight of Ni,
   from 1 to 3% by weight of Si,
   from 0.1 to 0.3% by weight of N,
   from greater than 0 to 0.15% by weight of C,
   from $\geq 0$ to 4% by weight of Mn,
   from $\geq 0$ to 4% by weight of Al,
   from $\geq 0$ to 0.05% by weight of P,
   from $\geq 0$ to 0.05% by weight of S, and
   from >0 to 0.1% by weight of one or more rare earth metals, and,
   apart from these, Fe and impurities resulting from production, the percentages each being based on the total weight.

2. A shell E according to claim 1 whose interior I comprises at least one dehydrogenation catalyst.

3. A shell E according to claim 1 whose interior I comprises at least one grid.

4. A shell E according to claim 1 which has an annular segment R.

5. A shell E according to claim 4 where the ratio of $V_1$=D:A, formed from half D of the difference between the external diameter A and the internal diameter of the annular segment R, is from 1:10 to 1:1000.

6. A shell E according to claim 5 where $V_1$ is from 1:40 to 1:500.

7. A shell E according to claim 4 where the ratio $V_2$=H:A, formed from the separation H of the two parallel circular planes delimiting the annular segment R and the external diameter A of the annular segment is >1.

8. A shell E according to claim 5 where the ratio $V_2$=H:A, formed from the separation H of the two parallel circular planes delimiting the annular segment R and the external diameter A of the annular segment is >1.

9. A shell E according to claim 6 where the ratio $V_2$=H:A, formed from the separation H of the two parallel circular planes delimiting the annular segment R and the external diameter A of the annular segment is >1.

10. A shell E according to claim 4 where the ratio $V_2$=H:A, formed from the separation H of the two parallel circular planes delimiting the annular segment R and the external diameter A of the annular segment is $\leq 1$.

11. A shell E according to claim 5 where the ratio $V_2$=H:A, formed from the separation H of the two parallel circular planes delimiting the annular segment R and the external diameter A of the annular segment is $\leq 1$.

12. A shell E according to claim 6 where the ratio $V_2$=H:A, formed from the separation H of the two parallel circular planes delimiting the annular segment R and the external diameter A of the annular segment is $\leq 1$.

13. A shell E according to claim 1 which has a hollow spherical zone segment K, within the interior I.

14. A shell E according to claim 1 which has thermal insulation material on its side facing away from the interior I.

15. The shell E according to claim 1 where the steel S has been alonized, alitized and/or aluminized on the side in contact with the interior I.

16. A process for heterogeneously catalyzed partial dehydrogenation of a hydrocarbon, which comprises performing the process in the interior I of a shell E according to claim 1.

* * * * *